United States Patent [19]

Warriner

[11] Patent Number: Plant 6,070

[45] Date of Patent: Dec. 29, 1987

[54] ROSE PLANT JACLAM

[75] Inventor: William A. Warriner, Tustin, Calif.

[73] Assignee: Jackson & Perkins Company, Medford, Oreg.

[21] Appl. No.: 817,566

[22] Filed: Jan. 10, 1986

[51] Int. Cl.[4] ..... A01H 5/00

[52] U.S. Cl. ..... Plt./28

[58] Field of Search ..... Plt./18–20, Plt./28, 29

*Primary Examiner*—James R. Feyrer

*Attorney, Agent, or Firm*—Manford R. Haxton

[57] ABSTRACT

A floribunda rose variety having very upright, vigorous growth habit, lustrous dark green foliage, attractive bright red flower color and exceptional production of cut flower.

1 Drawing Figure

This present invention relates to a new and distinct variety of rose plant of the floribunda class which was originated by crossing an unnamed variety with the variety Samantha, U.S. Plant Pat. No. 3,727.

The primary objective of this breeding was to produce a new rose variety of the floribunda class exhibiting high greenhouse cut flower production and bright red flower color. This objective was substantially achieved along with other desirable improvements as evidenced by the following unique combination of characteristics which are outstanding in the new variety and which distinguish it from its parents as well as from all other varieties of which I am aware:

1. Heavy and continuous cut flower production;
2. Attractive bright red flowers;
3. Upright growth habit;
4. Dark green foliage; and
5. Petal count of approximately 30.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Samantha, U.S. Plant Pat. No. 3,727.

Classification:

*Botanical.*—Rosa hybrid.

*Commercial.*—Floribunda.

FLOWER

Observations made from specimens grown in a greenhouse at Irvine, Calif. in August, 1985.

Blooming habit: Continuous.

Bud:

*Size.*—1"–1¼" when petals start to unfurl.

*Form.*—Short, blunt top.

*Color.*—When sepals first divide, deep red, Red Group 45B; when half blown, upper side of petals Red Group 45B; lower side of petals Red Group 45B.

*Sepals.*—Color: Green Group 143B. Three appendaged sepals normally to heavily appendaged. Two unappendaged sepals hairy edge.

*Receptacle.*—Color: Green Group 138B. Shape: Funnel. Size: Small. Surface: Smooth.

*Peduncle.*—Length: Medium. Surface: Smooth. Color: Medium green. Strength: Stiff, erect.

Open bloom:

*Size.*—Medium. Average open size 2½"–3".

*Borne.*—Singly to several together.

*Stems.*—Medium.

*Form.*—When first open, high center. Permanence: Retains its form to the end.

*Petalage.*—Number of petals under normal conditions: 30.

*Color.*—Center of flower: Upper side of petals, Red Group 45B; reverse side of petals, Red Group 45B. Base of petals, small whitish area. Major color: Red Group 45B.

*Variegations.*—Occasional white streak.

*Fragrance.*—Slight.

Petals:

*Texture.*—Thick.

*Shape.*—Round.

*Form.*—Tips slightly recurved.

*Arrangement.*—Imbricated.

*Persistence.*—Drop off cleanly.

*Lastingness.*—On the plant, long. As cut flower, long.

Reproductive parts:

*Anthers.*—Medium. Color: Yellow. Arrangement: Regular around styles and mixed with petaloids.

*Filaments.*—Color: White.

*Pollen.*—Lemon yellow.

*Styles.*—Color: Red.

*Stigmas.*—Color: White.

PLANT

Form: Bush.

Growth: Vigorous.

Foliage:

*Number of leaflets on normal mid-stem leaves.*—5 to 7.

*Size.*—Medium.

*Quantity.*—Normal.

*Color.*—New foliage: Red. Old foliage: Dark green (Green Group 139A).

Leaflets:

*Shape.*—Oval pointed.

*Texture.*—Smooth.

*Edge.*—Serrated.

*Serration.*—Single, small.

*Petiole.*—Rachis: Color: Green. Underside: Rough with prickles.

*Stipules.*—Medium, bearded.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Green and red.

Small prickles:

*Quantity.*—On main stalks, few. On laterals, few.

*Color.*—Green.

I claim:

1. A new and distinct variety of rose plant of the floribunda class, substantially as herein shown and described, characterized particularly as to novelty by the unique combination of its very upright, vigorous growth habit, lustrous dark green foliage, attractive bright red flower color and its exceptional production of cut flower.

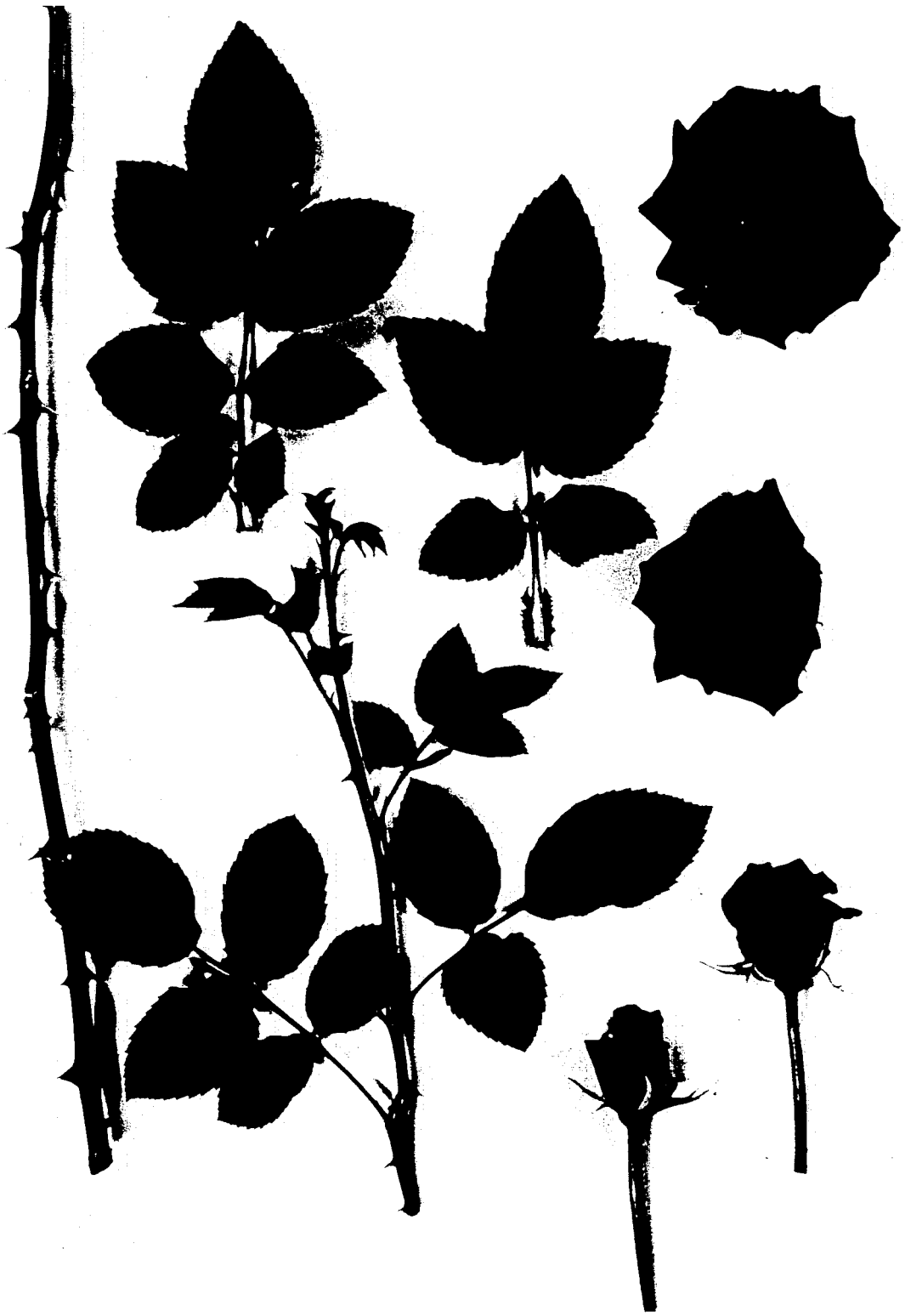

* * * * *